United States Patent [19]

Okada et al.

[11] Patent Number: 5,653,677
[45] Date of Patent: Aug. 5, 1997

[54] ELECTRONIC ENDOSCOPE APPARATUS WITH IMAGING UNIT SEPARABLE THEREFROM

[75] Inventors: Fujio Okada; Shigeo Suzuki, both of Omiya, Japan

[73] Assignee: Fuji Photo Optical Co. Ltd, Omiya, Japan

[21] Appl. No.: 416,349

[22] Filed: Apr. 4, 1995

[30] Foreign Application Priority Data

Apr. 12, 1994 [JP] Japan .................. 6-099266
Apr. 12, 1994 [JP] Japan .................. 6-099267
Apr. 12, 1994 [JP] Japan .................. 6-099268

[51] Int. Cl.⁶ .................................................. A61B 1/05
[52] U.S. Cl. .................. 600/112; 600/113; 600/173; 600/111
[58] Field of Search ............... 600/109–113, 129, 600/166, 172, 173; 348/45, 65

[56] References Cited

U.S. PATENT DOCUMENTS

| | | | |
|---|---|---|---|
| 4,895,138 | 1/1990 | Yabe | 600/110 |
| 4,918,521 | 4/1990 | Yabe et al. | 600/109 |
| 5,025,778 | 6/1991 | Silverstein et al. | 600/109 |
| 5,166,787 | 11/1992 | Irion | 348/65 |
| 5,305,121 | 4/1994 | Moll | 348/45 |
| 5,368,015 | 11/1994 | Wilk | 600/109 |

FOREIGN PATENT DOCUMENTS 9315648 8/1993 WIPO .................. 600/136

*Primary Examiner*—Richard J. Apley
*Assistant Examiner*—John P. Leubecker
*Attorney, Agent, or Firm*—Ronald R. Snider

[57] ABSTRACT

An electronic endoscope apparatus has an imaging unit separable from the distal end portion of an endoscope and is capable of easily handling and operating the separated imaging unit. In the apparatus, the imaging unit having an imaging device is arranged as a separate member so that the imaging unit can be separated from the distal end portion of the endoscope, and the imaging unit is held in the accommodating pocket of the endoscope by holding means such as, for example, an electromagnet or the like. Therefore, the imaging unit is separated from the distal end portion of the endoscope by turning off the electromagnet when the endoscope is inserted into a desired position of an observing subject and can carry out picking-up operation as an imaging unit independently of the endoscope. An electric signal is transmitted between an endoscope main body and the imaging unit as a radio wave through antennas. Observing means may be provided with the endoscope main body independently of the imaging unit and further a stereoscopic image may be formed by the imaging unit and the observing means. In addition, a wire can be disposed in the endoscope main body to hold the imaging unit in the accommodating unit as well as collect the separated imaging unit to the accommodating pocket. Moreover, when the wire is also used as a signal line, a signal transmission can be realized by a simple arrangement.

4 Claims, 7 Drawing Sheets

ELECTRONIC ENDOSCOPE APPARATUS WITH IMAGING UNIT SEPARABLE THEREFROM

BACKGROUND OF THE INVENTION

This application claims the priority of Japanese Patent Applications Nos. 6-99266, 6-99267 and 6-99268 filed in Apr. 12, 1994.

1. Field of the Invention

This invention relates to an electronic endoscope apparatus, and more specifically, to an electronic endoscope apparatus arranged such that an imaging unit can be separated from an endoscope main body in a body cavity.

2. Description of the Related Art

There is known an electronic endoscope apparatus for observing an image in an observing subject by a charge coupled device (CCD) as a solid imaging device, and in the electronic endoscope apparatus a diseased part of a body cavity such as a digestive tract and the like is observed and treated by inserting an electronic endscope into an observing subject. The inserting portion of the electronic endoscope is composed of a distal end portion on which the CCD is mounted, an angle portion which can bent in the upward, downward, right and left directions by operating an operating unit and a soft portion, and the distal end portion can be bent to a desired position by the angle portion.

However, the above electronic endoscope apparatus has a problem that since an observing subject is observed within a range regulated by the bending angle of the angle portion, there arises a range which cannot be observed. That is, it is difficult to bend the front surface of the distal end portion toward the backside of an inserting direction and for example, a projection such as a polyp cannot be observed from the backside thereof. Further, the conventional apparatus is arranged such that the positional relationship between an observing direction of a CCD and a direction toward which a treating tool is taken out from a treating tool inserting channel cannot be changed. When a diseased part is to be treated, however, the part is often treated more easily when the positional relationship between the observing direction and the treating tool taking-out direction is changed, and it is convenient if a diseased part can be observed from any arbitrary direction other than a treating direction.

Incidentally, it is contemplated to put a capsule-shaped micromachine with an observing unit alone into a patient through his or her mouth to realize unrestricted observation. However, when the micromachine is used alone, it must be moved to a diseased part by driving means provided with the apparatus itself while making use of the function of an organism and a problem arises in that the movement of the apparatus is not easy.

SUMMARY OF THE INVENTION

A first object of the present invention made by taking the above problems into consideration is to provide an electronic endoscope apparatus capable of observing an observing subject from any arbitrary direction regardless of a direction in which the distal end portion of an endoscope is operated and having an imaging unit which is separable from the main body of the apparatus so that the imaging unit can be easily moved and disposed.

To achieve the above first object, an electronic endoscope apparatus with an imaging unit separable therefrom according to the present invention is characterized by comprising the imaging unit having an imaging device and arranged as a separate member so as to be separated from the distal end portion of an endoscope, holding means for holding the imaging unit on the distal end portion, and electric signal transmitting means for mutually transmitting an electric signal between the imaging unit separated from the endoscope and a circuit attached to said endoscope.

There may be provided transmitting/receiving antennas disposed to the imaging unit and to the distal end portion of the endoscope and transmitting/receiving means for transmitting and receiving an electric signal through the antennas as the electric signal transmitting means.

An electromagnet and an electric conductive plate may be disposed or intake means using an air/water supply pipe, a treating tool inserting channel and the like may be used as the holding means. Further, operation for separating the imaging unit may be supported by air or water supplied through the air/water supply pipe. Further, a flagellum driving unit, a caterpillar (commodity name) driving unit and the like may be provided with the imaging unit as self-propelling means or self-position correcting means.

With the aforesaid arrangement, the imaging unit is connected to an endoscope main body by, for example, the electromagnet and then separated therefrom by turning off the electromagnet when the imaging unit is inserted and moved to a desired position in an observing subject. With this operation, the imaging unit served hitherto as an eye on the distal end portion of the endoscope picks up an image in the observing subject as an independent imaging unit separated from the endoscope. An image signal obtained by the imaging unit is subjected to predetermined processings and transmitted to the endoscope main body from a transmitter. The image signal is received by the receiver of the endoscope main body through the antenna disposed to the distal end portion. An image in the observing subject is displayed on a monitor in response to the received imaged signal after the signal is subjected to predetermined signal processings.

In the endoscope with the separable imaging unit, it is convenient if the separated imaging unit can be confirmed from the endoscope main body side. Further, if the interior of the observing subject can be observed by the combination of the endoscope main body with the separated imaging unit, a more easy-to-use apparatus can be obtained.

A second object of the present invention is to provided an electronic endoscope apparatus with an imaging unit separable therefrom capable of confirming the imaging unit when it is separated from the distal end portion of an endoscope as well as observing the interior of an observing subject in cooperation with the imaging unit.

To achieve the second object, the present invention is characterized in the provision of observing means for optically or electrically observing the interior of an observing subject through an observing window disposed to the distal end portion in addition to the above basic constituting elements. Optical observing means using an optical fiber and an imaging unit having an imaging device can be used as the observing means. When the imaging unit is used, a stereoscopic image can be formed by the imaging unit attached to the main body and the separable imaging unit.

According to the above arrangement, there can be obtained an advantage that the confirmation of the separated imaging unit and the positional correction thereof are easily carried out and further a diseased part can be easily observed and treated by the cooperation of the separated imaging unit and the imaging unit attached to the main body. Further, when an electric imaging unit is used as the observing means and the separable imaging unit is not separated, a stereoscopic image can be displayed on a monitor in response to image information obtained by the separable imaging unit and the imaging unit attached to the main body after the image information is subjected to stereoscopically observing processing.

It is convenient if the separated imaging unit is moved and disposed without using special driving means such as self-propelling means and the like, and further if the imaging unit can be promptly collected on the completion of observation and treatment, an easy-to-use apparatus can be obtained.

A third object of the present invention is to provide an apparatus capable easily moving and disposing a separated imaging unit and further easily and simply collecting the separated imaging unit.

To achieve the third object, the present invention is characterized by comprising an imaging unit having an imaging device and arranged as a separate member so as to be separated from the distal end portion of an endoscope, wire holding means for holding the imaging unit in the accommodating unit attached to an endoscope by a wire connected to the imaging unit and disposing the wire in the main body of the endoscope as well as collecting the imaging unit separated from the endoscope into the accommodating unit by stretching the wire, and electric signal transmitting means for mutually transmitting an electric signal between the imaging unit separated from the endoscope and the circuit in said endoscope.

With the above arrangement, the imaging unit is connected and fixed to the accommodating unit by stretching the wire and then separated therefrom by loosening the wire when the endoscope is inserted and moved to a desired position in an observing subject. On the completion of observation and treatment, the imaging unit is accommodated in the accommodating unit by stretching the wire, so that the imaging unit can be simply and promptly-collected.

Although an image signal obtained by the imaging unit may be transmitted to an endoscope main body by a wireless system similarly to the above, a signal line may be also disposed in the wire, and in this case there is an advantage that a signal transmission can be realized with a simple arrangement. When the wire is also used as the signal line, an image signal obtained by the imaging unit is transmitted to the signal processing circuit attached to the endoscope through the signal line in the wire and subjected to predetermined signal processings in the circuit so as to display an image in an observing subject on a monitor. Therefore, the interior of the observing subject can be observed from a direction different from that in which the endoscope is inserted.

DESCRIPTION OF PREFERRED EMBODIMENTS

First Embodiment

Figure 1:
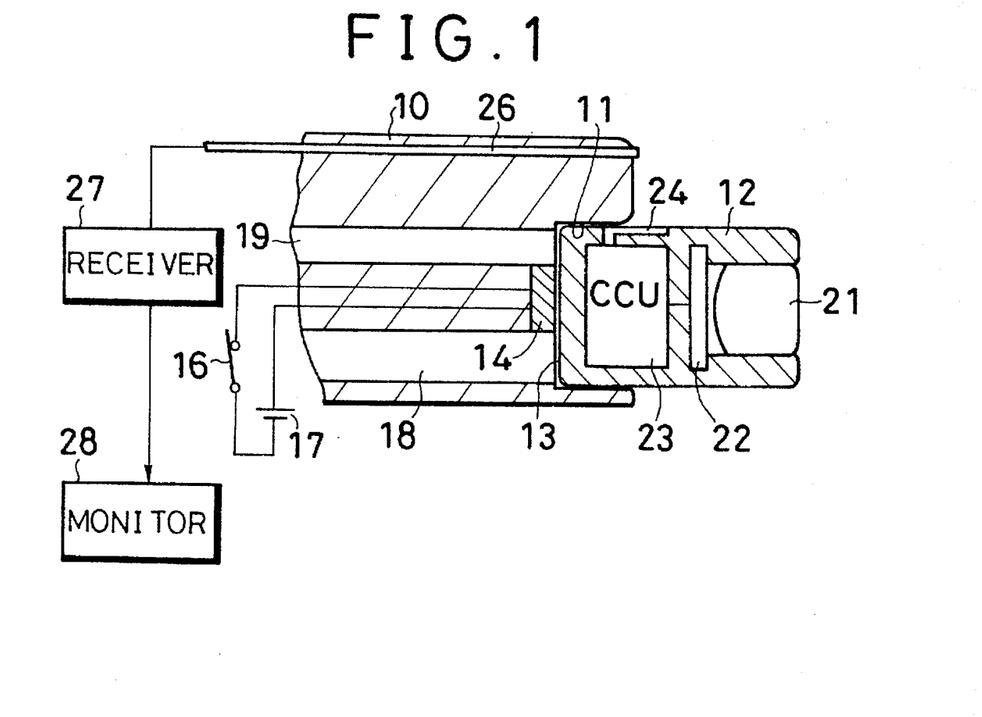
FIG. 1 is a view showing an arrangement of the distal end portion of an electronic endoscope apparatus according to a first embodiment of the present invention.
Figure 2:
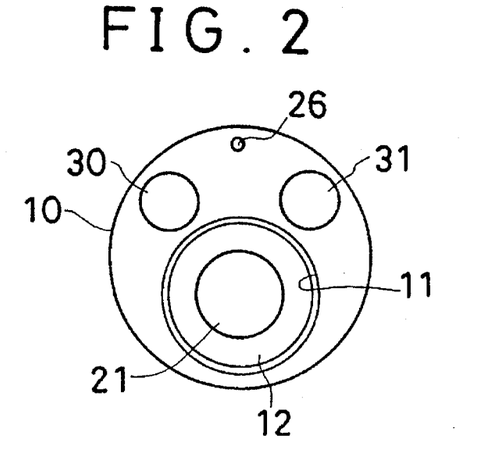
FIG. 2 is a view showing an arrangement of the front surface of a distal end portion of FIG. 1.

FIGS. 1 and 2 show an arrangement of an electronic endoscope apparatus with an imaging unit separable therefrom according to a first embodiment. In FIG. 1, an electronic endoscope has a distal end portion 10 to which a circular-groove-shaped accommodating unit 11 is defined and about a one third portion of an imaging unit 12 composed of a columnar capsule is accommodated in the accommodating pocket 11 and separably disposed therein. The imaging unit 12 has rear end surface 13 composed of a metal plate or the like as well as an electromagnet 14 is disposed on the bottom of the accommodating pocket 11 and an operation switch 16 and a power source 17 are connected to the electromagnet 14.

Further, the electronic endoscope includes a treating tool inserting channel 18 for inserting a treating tool such as a clamp and the like and an air/water supply path 19 each disposed thereto and the outlets of them are disposed to the bottom of the accommodating unit 11. Therefore, when the operation switch 16 turns off the electromagnet 14, the imaging unit 12 is separated from the accommodating pocket 11. At that time, however, it is also possible to fly the imaging unit 12 to a distant position by air or water supplied from the supply path 19. Note, the imaging unit 12 may be provided with a flagellum driving unit composed of a flagellum and driving member, a caterpillar driving unit or the like as self-propelling means or self-position correcting means.

A lens unit 21, a CCD 22 as a solid imaging device and a camera control unit (CCU) 23 including an image signal processing circuit and transmitting/receiving unit are disposed in the imaging unit 12 and an antenna 24 is disposed on the surface of the imaging unit 12. That is, an image in an observing subject is captured by the CCD 22 through the lens unit 21, an image signal obtained by the CCD 22 is subjected to predetermined processings such as an amplifying processing and the like in the CCU 23 and then modulated and the thus obtained transmitting image signal is output from the antenna 24.

On the other hand, an antenna 26 is disposed on the surface of the distal end portion 10 of the electronic endoscope and a monitor 28 is connected to the antenna 26 through a receiver 27. That is, an image signal input from the antenna 26 is demodulated by the receiver 27 and an image of an observing subject is displayed on the monitor 28 in response to the image signal. It is needless to say that a control signal necessary to the operation of the imaging unit 12 is transmitted thereto through a not shown transmitting circuit in the electronic endoscope. Further, as shown in FIG. 2, irradiating windows 30 and 31 are defined on the front surface of the distal end portion 10 and an illuminating light is supplied to the irradiating windows 30 and 31 from a not shown light source through a light guide.

Figure 3:
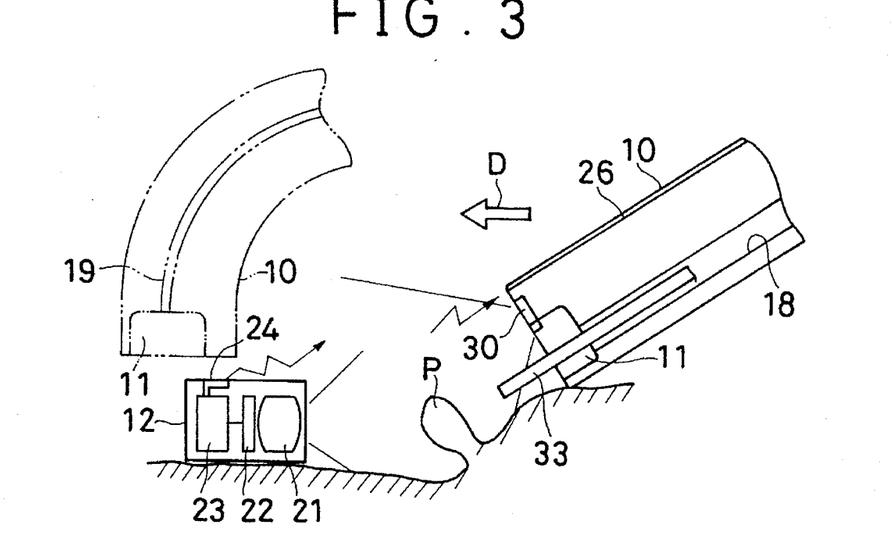
FIG. 3 is a view showing a state that the electronic endoscope apparatus of the first embodiment is applied to a body cavity.

The first embodiment is arranged as described above and operation of the embodiment will be described with reference to FIG. 3. First, as shown in FIG. 1, the distal end portion 10 of the electronic endoscope is inserted into a body cavity shown in FIG. 3 (inserting direction: D) in the state that the electromagnet 14 is turned on by the operation switch 16 and the imaging unit 12 is accommodated in the accommodating unit 11. For example, when a polyp P of FIG. 3 is desired to be observed from the backside thereof, the distal end portion 10 is inserted to the position shown by a chain line and the electromagnet 14 is turned off by the operation switch 16 to separate the imaging unit 12. The imaging unit 12 can be disposed so that the lens unit 21 thereof faces to the polyp P in such a manner that when the imaging unit 12 is released from the distal end portion 10, the distal end portion 10 is slightly pushed inward. When air or water is ejected from the air/water supply path 19 at that time, the imaging unit 12 can be moved forward or its position can be corrected. Further, when the imaging unit 12 is provided with the self-propelling means or the self-position correcting means, the imaging unit 12 can be disposed at a desired position by driving the flagellum, caterpillar or the like.

During the above operation, an image signal in an observing subject captured by the CCD 22 is modulated to a transmitting image signal in the imaging unit 12 and output from the antenna 24. On the other hand, the antenna 26 attached to the endoscope main body receives the above image signal which is demodulated by the receiver 27 and then supplied to the monitor 28. With this arrangement, an image of the polyp P and its vicinity is displayed on the monitor 28. Then, the distal end portion 10 is returned to, for example, the position of a solid line while the image on the monitor 28 being observed and a treating tool 33 is taken out from the treating tool inserting channel 18 at the position. Consequently, the polyp can be treated with the treating tool 33 while being observed from the backside thereof.

On the completion of the above observation and treatment, the separated imaging unit 12 in FIG. 3 can be collected by the following manner. More specifically, when the imaging unit 12 can be attracted into the accommodating unit 11 by the electromagnet 14 at the distal end portion 10 or when the imaging unit 12 can be moved into the accommodating unit by the self-propelling means, the imaging unit 12 is collected into the accommodating pocket 11 by the electromagnet or the self-propelling means. When the imaging unit 12 cannot be accommodated into the accommodating unit 11 in such a manner, a basket type clamp 34 shown in FIG. 4, a three-claw type clamp or the like is inserted through the treating tool inserting channel 18 to grip and collect the imaging unit with the clamp. Further, it is also possible to collect the imaging unit 12 which is left as it is by the discharging function of an organism.

In the above mentioned, the electronic endoscope shown in FIG. 1 may be used only to move and dispose the imaging unit 12 to a predetermined position in an observing subject. More specifically, it is possible that after the imaging unit 12 is disposed at the position shown in FIG. 3, the endoscope is extracted once and another electronic endoscope having an imaging unit integrally formed therewith is inserted to carry out a predetermined treatment while the polyp P is observed from the front side and backside thereof.

Second Embodiment

Figure 5:
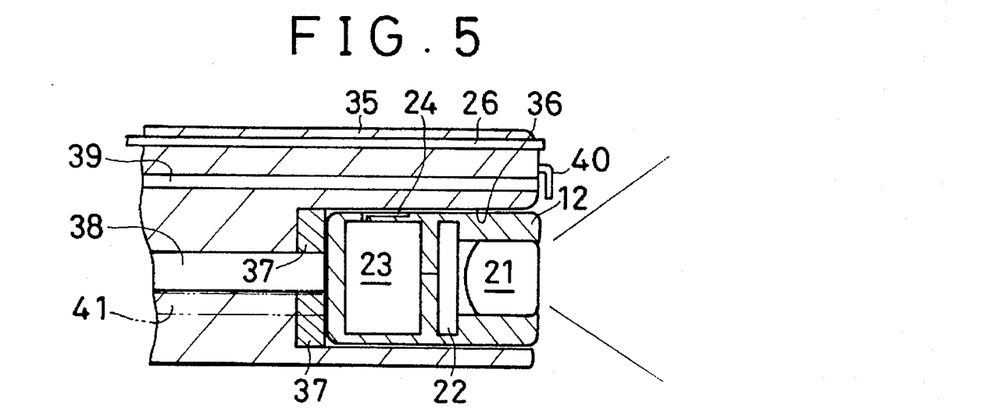
FIG. 5 is a view showing an arrangement of the distal end portion of a second embodiment.

FIG. 5 shows an arrangement of a second embodiment as another example of the accommodating unit for accommodating the imaging unit. In FIG. 5, although an imaging unit 12 is arranged similarly to the above imaging unit, an accommodating pocket 36 is formed to a distal end portion 35 to entirely accommodate the imaging unit 12 and an electromagnet 37 is attached on the bottom of the accommodating pocket 36. A treating tool inserting channel 38 is connected to the bottom. Further, an air/water supply path 39 is defined up to the front surface of the distal end portion 35 and a nozzle 40 is provided with the front surface. Therefore, the window of the lens unit 21 of the imaging unit 12 can be washed with air or water ejected from the nozzle 40. Note, an antenna 26 is also attached to the front surface likewise and a separate air/water supply path 41 may be connected to the bottom of the accommodating unit 36 similarly to the first embodiment.

According to the second embodiment, since the imaging unit 12 is entirely accommodated in the accommodating pocket 36, there is no possibility that the imaging unit 12 comes into contact with the wall of a body cavity and the like when the electronic endoscope is inserted. As a result, the electronic endoscope can be stably inserted. In this case, since the imaging unit 12 may not be easily separated only by turning off the electromagnet 37, the imaging unit 12 is taken out from the accommodating pocket 36 by a treating tool inserted through the treating tool inserting channel 38 or with air or water supplied from the supply path 41.

According to the above embodiments, although the electromagnet 14 or 37 is used as holding means of the imaging unit 12, the imaging unit 12 may be held by inspiring air through the air/water supply path 19 or 41 in the state that the imaging unit 12 is accommodated in the accommodating unit 11 or 36. In particular, in the case of the second embodiment, a sufficiently stable holding state can be obtained by the inspiration.

As described above, according to the above embodiments, an image can be independently picked up by the separated imaging unit and an observing subject can be observed from any arbitrary direction regardless a direction toward which the distal end portion of the endoscope is operated. Further, since the imaging unit is introduced into the observing subject by the endoscope, there is an advantage that the imaging unit can be smoothly moved and disposed.

Third Embodiment

Figure 6:
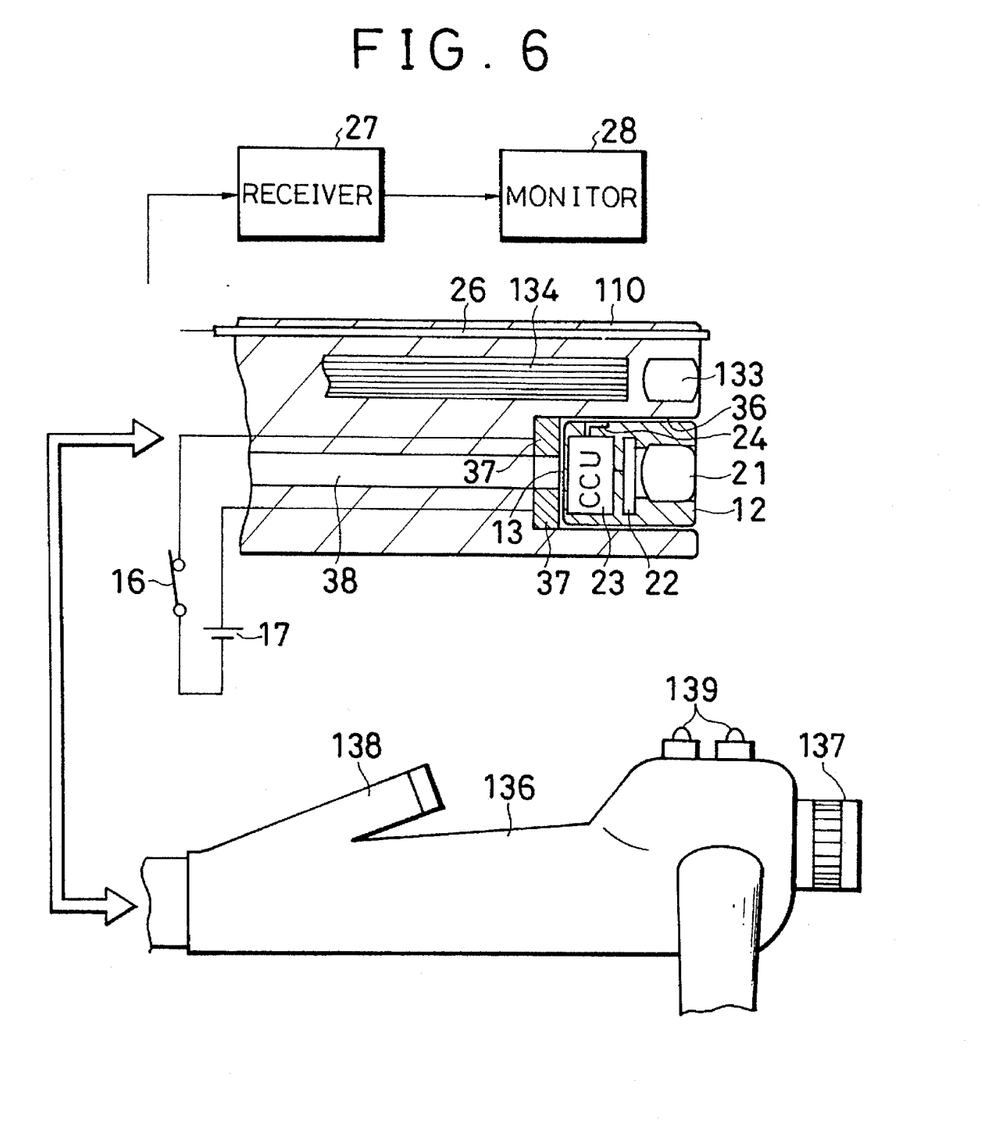
FIG. 6 is a view showing an arrangement of an electronic endoscope apparatus according to a third embodiment.
Figure 7:
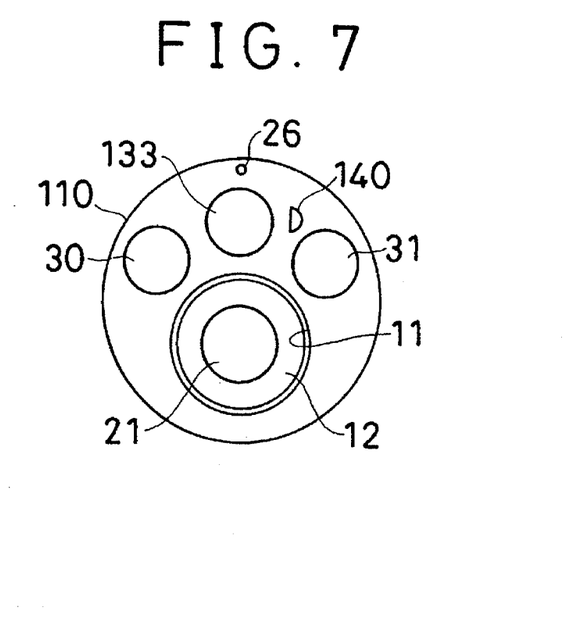
FIG. 7 is a view showing an arrangement of the front surface of a distal end portion of FIG. 6.

FIGS. 6 and 7 show an arrangement of a third embodiment wherein an imaging unit 12 composed of a columnar capsule is also separably accommodated in an accommodating pocket 36 disposed to the distal end portion 110 of an electronic endoscope similarly to the second embodiment. The same numerals as used in the above including the numeral 12 used to denote the imaging unit are used to denote the same parts in the third embodiment.

In the third embodiment, although the imaging unit 12 can be freely moved when an electromagnet 37 is turned off by an operation switch 16, the imaging unit 12 is taken out from the accommodating pocket 36 by being pushed with an operating member inserted through a treating tool inserting channel 38. However, the imaging unit 12 may be guided in such a manner that an air/water supply path is also disposed in the vicinity of the treating tool inserting channel 38 and air or water is supplied to the imaging unit 12 from the supply path. Further, the imaging unit 12 may be provided with a flagellum driving unit composed of a flagellum and driving member or a caterpillar (commodity name) driving unit as self-propelling means or self-position correcting means.

On the other hand, an image signal input from an antenna 26 is demodulated by a receiver 27 attached to an endoscope main body and an image in an observing subject is displayed on a monitor 28 in response to the image signal. Further, as shown in FIG. 7, an irradiating light is supplied to irradiating windows 30 and 31 disposed on the front surface of the distal end portion 110 from a light source through a light guide.

Optical observing means is provided with the endoscope main body of the third embodiment. More specifically, an observing window lens unit 133 is disposed to the distal end portion 110, an optical fiber 134 is connected to the observing window lens unit 133 and the eyepiece 137 of an operating unit 136. Therefore, an image in an observing subject captured through the observing window lens unit 133 can be observed through the eyepiece 137. Further, a treating tool inserting port 138 for the treating tool inserting channel 38 and an operation switch 139 for supplying air and water are provided with the above operating unit 136 and an air/water supply path is disposed in the endoscope as well as an air/water supply nozzle 140 is disposed in the vicinity of the observing window lens unit on the front surface of the distal end portion 133 as shown in FIG. 7. Washing and the like of the observing window lens unit 133 can be carried out by the air/water supply nozzle 140 by operating the operation switch 139.

Figure 8:
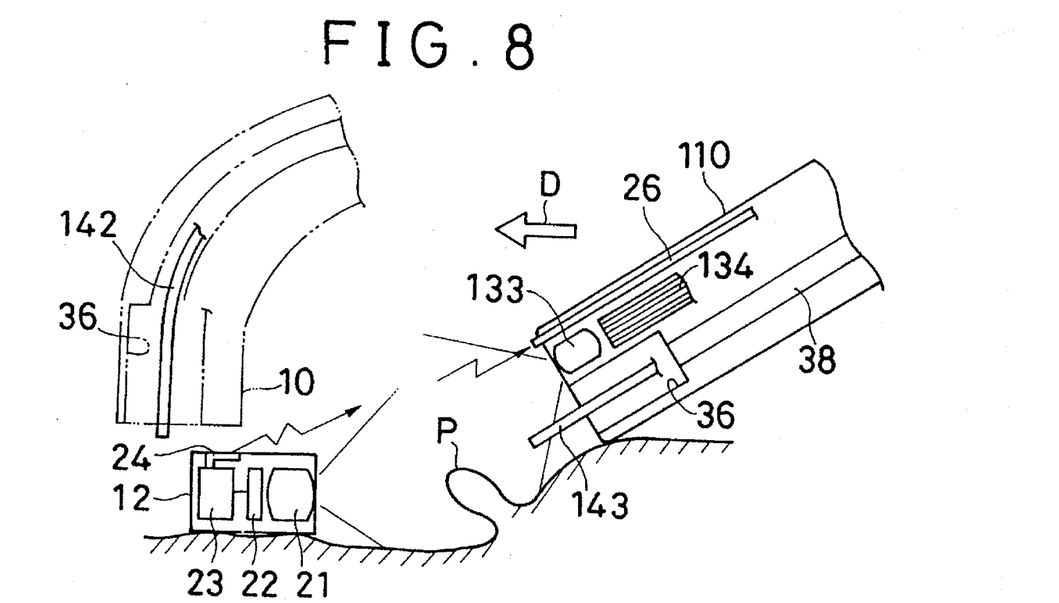
FIG. 8 is a view showing a state that the electronic endoscope apparatus of the third embodiment is applied to a body cavity.

The third embodiment is arranged as described above and operation of the embodiment will be described below with reference to FIG. 8. First, as shown in FIG. 6, the distal end portion 110 of the electronic endoscope is inserted into a body cavity (inserting direction: D) shown FIG. 8 in the state that the electromagnet 37 is turned on by the operation switch 16 and the imaging unit 12 is accommodated in the accommodating unit 36. When a polyp P shown in FIG. 8 is desired to be observed from the backside thereof, the distal end portion 110 is inserted to a chain line, then the electromagnet 37 is turned off by the operation switch 37 to separate the imaging unit 12. Then, when the distal end portion 110 is slightly pushed inward while the imaging unit 12 is pushed out with an operating member 142 inserted through the treating tool inserting channel 38, the lens unit 21 of the imaging unit 12 can be disposed so that it faces to the polyp P. The position of the imaging unit 12 at that time can be corrected by the above operating member 142.

Note, when the air/water supply path is disposed up to the accommodating pocket 36, the imaging unit 12 can be forwarded and the position thereof can be corrected by air or water ejecting from the supply path.

During the above operation, the interior of an observing subject can be observed through the observing wind lens unit 133 by looking though the eyepiece 137, whereby the imaging unit 12 can be easily located at a desired position or the backwardly of the polyp P in the case of FIG. 8. Further, image information of the interior of the observing subject captured by the imaging unit 12 is output from an antenna 24 as a radio wave and received by the antenna 26 and the receiver 27 so that it is displayed on the monitor 28 as an image. The imaging unit 12 enables an image of the backside and vicinity of the polyp P to be displayed on the monitor 28.

Then, the distal end portion 110 is returned to, for example, the position of a solid line while the eyepiece of the endoscope main body is looked through the image on the monitor 28 is observed and a treating tool 143 is taken out from the treating tool inserting channel 38. Consequently, a treatment can be carried out well with the treating tool 143 while the polyp P is observed from the front side (the inserting direction D) and the backside thereof in the case.

Figure 4:
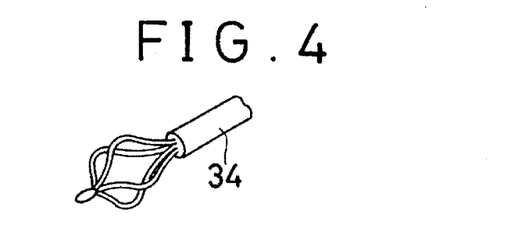
FIG. 4 is a view showing a basket type clamp used in the embodiment.

On the completion of the above observation and treatment, the separated imaging unit 12 shown in FIG. 8 can be collected using the basket type clamp 34 shown in FIG. 4, a three-claw type clamp or the like. It is needless to say that the imaging unit 12 can be collected by the electromagnet 37 on the distal end portion 110 or may be collected by the self-propelling means.

As described above, according to the third embodiment, since the separated imaging unit can be confirmed by the observing means, the imaging unit can be smoothly disposed and moreover there is an advantage that the interior of an observing subject can be observed by both the imaging unit and observing means at different angles.

Fourth Embodiment

Figure 9:
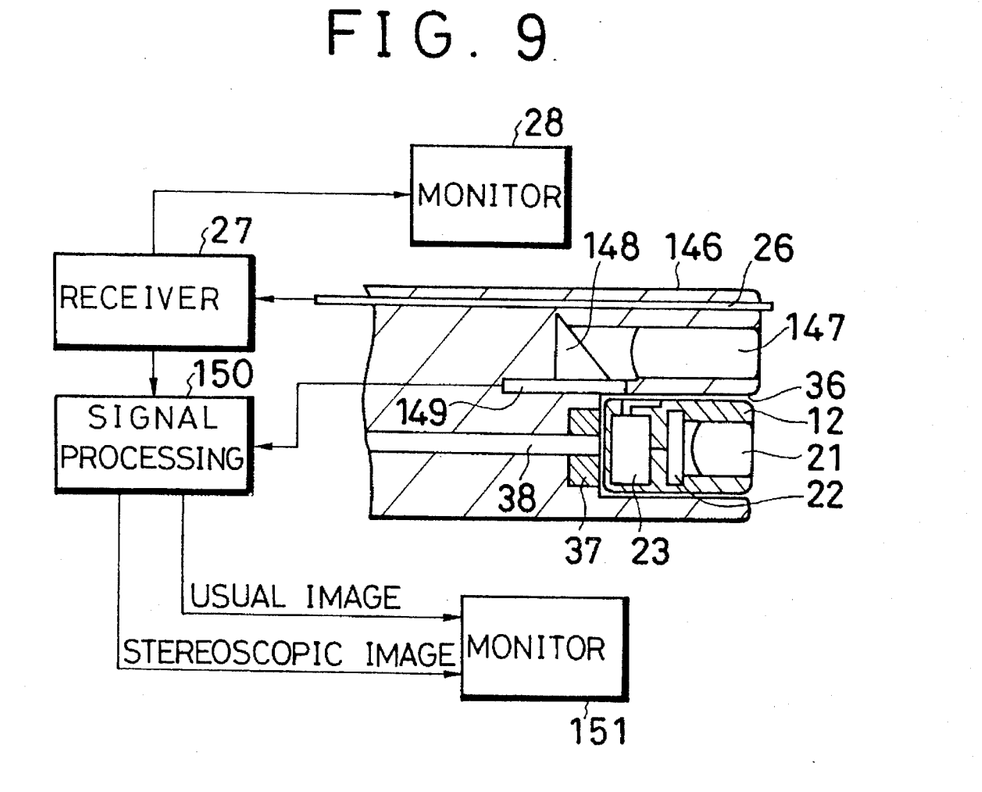
FIG. 9 is a view showing an arrangement of an apparatus of a fourth embodiment.

FIG. 9 shows an arrangement of a fourth embodiment capable of forming a stereoscopic image. In FIG. 9, although an imaging unit 12 is arranged similarly to the above, another imaging unit composed of a lens unit 147, a prism 148 and a CCD 149 is disposed to a distal end portion 146 in replace of the above optical observing means and has a positional relationship with the imaging unit 12 so that they can stereoscopically observe an observing object. The CCD 149 includes a signal processing circuit 150 for carrying out a usual image processing and a stereoscopically observed image processing and a monitor 151 is connected to the signal processing circuit 150.

According to the arrangement of the fourth embodiment, a signal processing is usually carried out with respect to an image signal output from the CCD 149 and an image in an observing subject is displayed on a monitor 151. Further, an image in the observing subject is displayed on a monitor 28 in response to an image signal received by a receiver 27 in the imaging unit 12. On the other hand, the image signal received by the receiver 27 is also supplied to the above signal processing circuit 150. Thus, when a stereoscopic image is selected by an operating unit or the like, the signal processing circuit 150 carries out the stereoscopic signal processing based on the image signal input from the receiver 27 and an image signal input from the CCD 149. Consequently, according to the fourth embodiment, when the imaging unit is not separated, an stereoscopic image in an observing subject can be observed on the monitor 151.

Fifth Embodiment

Figure 10:
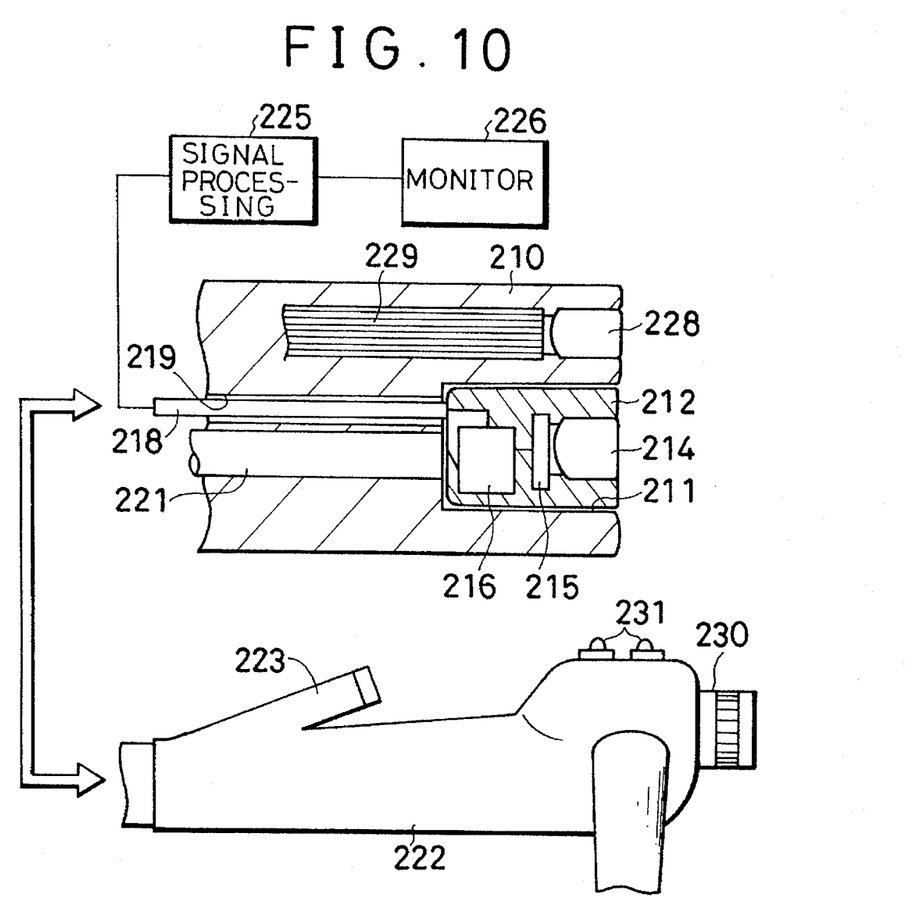
FIG. 10 is a view showing an arrangement of an electronic endoscope apparatus according to a fifth embodiment.
Figure 11:
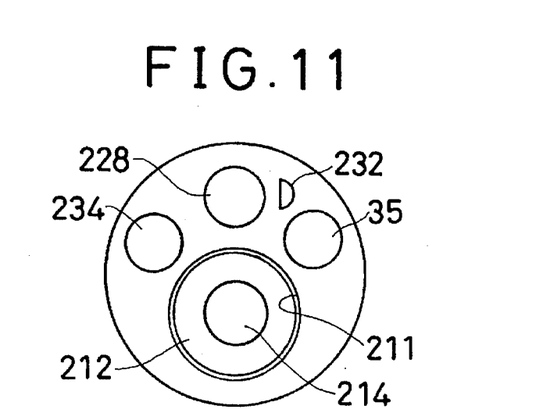
FIG. 11 is a view showing an arrangement of the front surface of a distal end portion of FIG. 10.

FIGS. 10 and 11 show an arrangement of a fifth embodiment of an electronic endoscope apparatus with a separable imaging unit. In FIG. 10, an imaging unit 212 composed of a columnar capsule is separably accommodated in an accommodating pocket 211 on the distal end portion 210 of an electronic endoscope and a lens unit 214, a CCD 215 and a signal processing circuit 216 are disposed in the imaging unit 212 similarly to the above embodiments.

A wire 218 containing a signal line is connected to the imaging unit 212. The wire 218 is passed through a wire guide 219 attached to the distal end portion 210. The wire 218 is a single wire or a strand wire composed of a metal material, plastic material or the like containing the signal line and arranged as a flexible wire. Further, a treating tool inserting channel 221 for introducing a treating tool such as a clamp or the like is disposed from the above accommodating unit 211 to the treating tool and wire inserting port 223 of an operating unit 222 and the wire guide 219 is connected to the treating tool and wire inserting port 223 through a junction. More specifically, the wire 218 extends to the treating tool and wire inserting port 223 in the state that the signal wire contained therein is separated at the junction. On the other hand, the length of the signal line can be changed in such a manner, for example, that the signal line is loosened (wound) or a sliding contact member or the like is used.

A signal processing circuit 225 and a monitor 226 are connected to the signal line in the above wire 218. An image sinal obtained by the CCD 215 is subjected to processings such as a gamma compensation processing and the like in the signal processing circuit 225 and an image in an observing subject is displayed on the monitor 226 in response to an output from the signal processing circuit 225.

Further, an optical observing means is provided with the endoscope main body of the fifth embodiment. More specifically, an optical fiber 229 is connected to an observing window lens unit 228 disposed to the distal end portion 210 and also to the eyepiece 230 of an operating unit 222. Thus, an image in the observing subject can be observed through the eyepiece 230. Further, an operation switch 231 for supplying air and water is provided with the operating unit 222, an air/water supply path is disposed in the endoscope as well as an air/water supply nozzle is disposed in the vicinity of the observing wind lens unit 228 on the front surface of the distal end portion as shown in FIG. 11. Washing and the like of the observing window lens unit 228 can be carried out by the air/water supply nozzle 232 through the operation switch 231. As shown in FIG. 11, irradiating windows 234, 235 are disposed on the front surface of the distal end portion 210.

Figure 12:
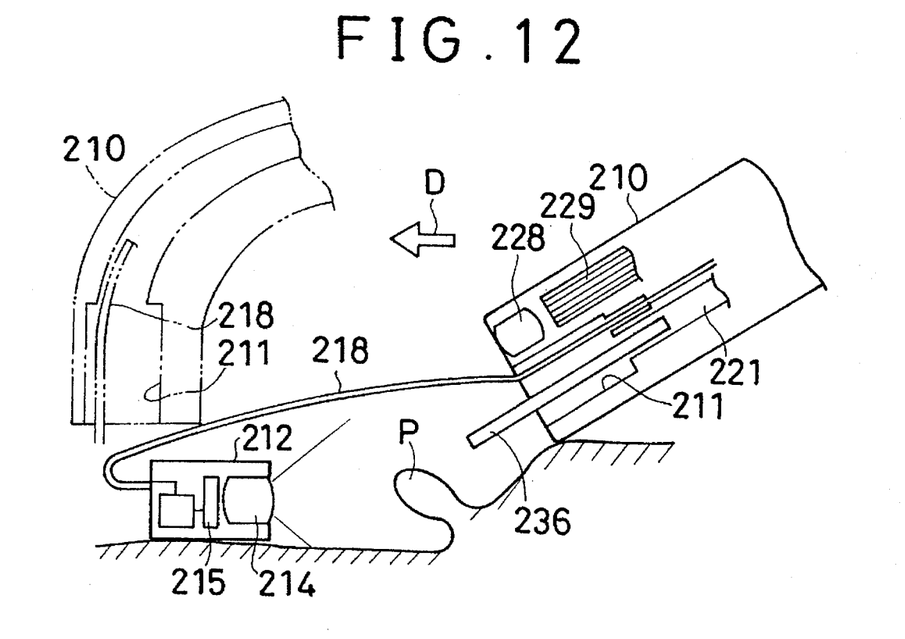
FIG. 12 is a view showing a state that the electronic endoscope apparatus of the fifth embodiment is applied to a body cavity.

The fifth embodiment is arranged as described above and operation of the embodiment will be described with reference to FIG. 12. First, as shown in FIG. 10, when the wire 218 is stretched, the distal end portion 210 of the electronic endoscope is inserted into a body cavity of FIG. 12 (inserting direction: D) in the state that the imaging unit 212 is accommodated in the accommodating pocket 211. For example, when a polyp P of FIG. 12 is desired to be observed from the backside thereof, the distal end portion 210 is inserted up to the position of a chain line and then the wire 218 is loosened to separate the imaging unit 212 from the distal end portion 210. The imaging unit 212 can be disposed so that the lens unit 214 thereof faces toward the polyp P in such a manner that when the imaging unit 212 is released from the distal end portion 210, the distal end portion 210 is slightly pushed inward. It is possible here to correct the position of the imaging unit 212 by taking out an operating member from the treating tool inserting channel 221.

During the above operation, the interior of an observing subject can be observed through the observing wind lens unit 228 by looking though the eyepiece 230 of the operating unit 222, whereby the imaging unit 212 can be located at a desired position or backwardly of the polyp P in the case of FIG. 10. Further, an image signal of the interior of the observing subject captured by the CCD 215 is subjected to an amplifying processing and the like by the signal processing circuit 216 also in the imaging unit 212 and an output from the signal processing circuit 216 is supplied to the signal processing circuit 225 attached to the endoscope main body through the signal line in the wire 218. Image processings such as a gamma processing and the like are carried out by the signal processing circuit 225 and an image in the observing subject is displayed on the monitor 226. Therefore, according to the imaging unit 212, the image of the polyp P and its vicinity is displayed on the monitor 226.

Next, the distal end portion 210 is returned to, for example, the position of a solid line while the eyepiece 230 is looked through or the image on the monitor 226 is observed and a treatment can be carried out at the position with a treating tool 236.

On the completion of the observation and treatment, the separated imaging unit 212 shown in FIG. 12 is attracted to and accommodated in the accommodating pocket 211 by the wire 218 stretched through the treating tool and wire inserting port 223. With this arrangement, the imaging unit 212 can be promptly and simply collected on the completion of the observation and treatment without making use of the discharging function and the like of an organism.

Sixth Embodiment

Figure 13:
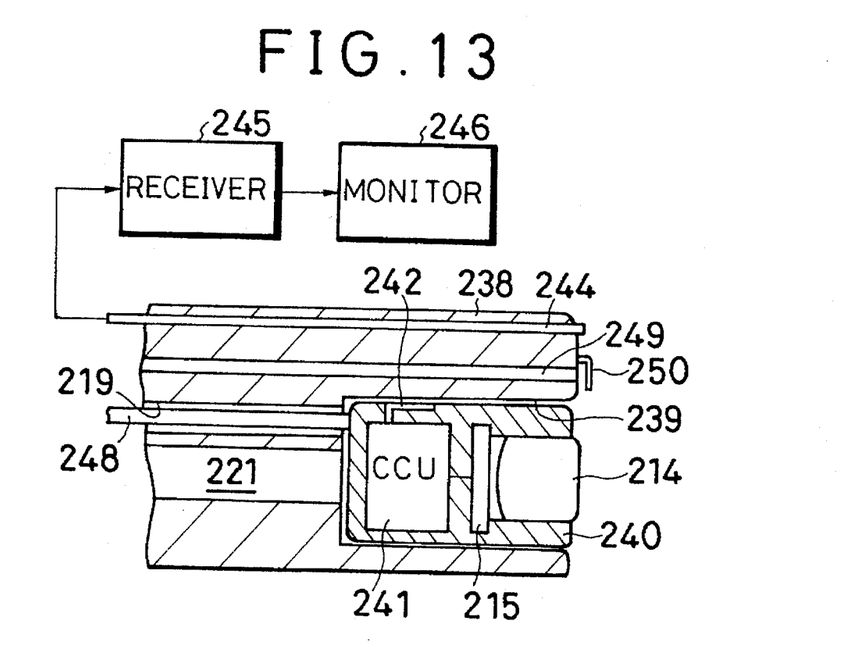
FIG. 13 is a view showing an arrangement of an apparatus of a sixth embodiment.

FIG. 13 shows an arrangement of a sixth embodiment which is an example for transmitting a signal by a wireless system and not using optical observing means. In FIG. 13, an imaging unit 240 disposed in an accommodating unit 239 on an distal end portion 238 contains a camera control unit (CCU) 241 having an image signal processing circuit and a transmitting unit and an antenna 242 is disposed on the surface of the imaging unit 240. An image signal obtained by a CCD 215 is subjected to an image processing by the CCU 241 and then converted into a transmitting signal which is output from an antenna 242.

On the other hand, an antenna 244 is disposed on the surface of the distal end portion 238 in an electronic endoscope and a monitor 246 is connected to the antenna 244 through a receiver 245. A wire 248 is connected to the imaging unit 240 similarly to the fifth embodiment, and in this case, the wire 248 does not also serve as a signal line. Further, an air/water supply path 249 is formed up to the front surface of the distal end portion 238 and a nozzle 250 is provided on the front surface. Therefore, the window of the lens unit 241 of the imaging unit 240 can be washed with air or water ejected from the nozzle 250.

According to the sixth embodiment, an image signal captured by the imaging unit 240 is modulated by the CCU 241 and output from the antenna 242, whereas the image signal received through the antenna 244 is demodulated by the receiver 245 and supplied to the monitor 246. With this arrangement, the imaging unit 240 enables an image of the backside and the like of the polyp P shown in FIG. 12 to be displayed on the monitor 246. On the completion of observation and treatment carried out through the image, the imaging unit 240 is promptly collected by the operation of the wire 248.

What is claimed is:

1. An electronic endoscope apparatus comprising:

an endoscope having a distal end portion;

an imaging unit disposed on the distal end portion and including an imaging device and a lens;

means for holding said imaging unit on said distal end portion, wherein said means for holding includes an electromagnet and an electroconductive plate;

means for separating said imaging unit from said distal end portion such that said imaging device is provided with omnidirectional free movement; and electric signal transmitting means for mutually transmitting an electric signal between said imaging unit and said endoscope.

2. An electronic endoscope apparatus according to claim 1, wherein said electric signal transmitting means comprises a first antenna disposed on said imaging unit, a second antenna disposed on said distal end portion, and a transmitting/receiving means disposed on said imaging unit for transmitting and receiving said electric signal through said first and second antennas.

3. An electronic endoscope apparatus according to claim 1, wherein said means for separating comprises a supply means for supplying air or water to said distal end portion.

4. An electronic endoscope apparatus according to claim 1, further including an observation means disposed on said distal end portion for forming an image, said observation means including a second imaging unit having an imaging device;

wherein a stereoscopic image is formed by said observation means and said imaging unit when said imaging unit is held on the distal end portion by said means for holding.

* * * * *